(12) United States Patent
Shimakawa et al.

(10) Patent No.: US 7,141,132 B2
(45) Date of Patent: Nov. 28, 2006

(54) PROCESS FOR MAKING DISPOSABLE WEARING ARTICLE

(75) Inventors: Taiji Shimakawa, Kagawa-ken (JP); Yoshitaka Mishima, Kagawa-ken (JP); Tomoko Sugito, Kagawa-ken (JP); Kaiyo Nakajima, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 507 days.

(21) Appl. No.: 10/733,573

(22) Filed: Dec. 12, 2003

(65) Prior Publication Data

US 2004/0118505 A1     Jun. 24, 2004

(30) Foreign Application Priority Data

Dec. 13, 2002  (JP) ............................ 2002-362501

(51) Int. Cl.
*A61F 13/15*     (2006.01)
(52) U.S. Cl. ................. 156/204; 156/211; 156/226; 156/227; 156/252; 156/267
(58) Field of Classification Search .................... None
See application file for complete search history.

(56) References Cited

U.S. PATENT DOCUMENTS 2,122,417 A * 7/1938 Fridolph ..................... 604/386
3,794,033 A * 2/1974 Ryan ........................... 604/365
4,690,719 A    9/1987 Lucas et al.
2004/0153043 A1* 8/2004 Sugito et al. .......... 604/385.27

FOREIGN PATENT DOCUMENTS

| EP | 216164 A1 | 4/1987 |
| JP | 10-513070 | 12/1998 |
| WO | 9600117 | 1/1996 |

\* cited by examiner

*Primary Examiner*—Richard Crispino
*Assistant Examiner*—Barbara J Musser
(74) *Attorney, Agent, or Firm*—Lowe Hauptman & Berner LLP

(57) ABSTRACT

An elastically stretchable disposable wearing article has a front waist region, a rear waist region and a crotch region. This wearing article is formed with a first elastic zone, a second elastic zone and third elastic zones respectively exhibiting stretch stress adjusted to be decreased in this order. An elastically stretchable web is continuously fed in a machine direction, formed with pairs of slits in desired patterns so that two slits constituting each of the pairs may be symmetrically laid about a transversely middle zone of the web and then folded in a cross direction orthogonal to the machine direction so that the web may be alternately overlapped on itself about the transversely middle zone to form the wearing article.

4 Claims, 11 Drawing Sheets

PROCESS FOR MAKING DISPOSABLE WEARING ARTICLE

BACKGROUND OF THE INVENTION

The present invention relates to processes for making a 5 disposable wearing article having elastically stretchable. The present invention is based on, and claims priority from, Japanese Application Serial No. 2002-362501, filed Dec. 13, 2002, the disclosure of which is hereby incorporated by reference herein in its entirety.

In the art of disposable wearing articles such as disposable diapers, it is well known to provide its crotch region with an elastically stretchable properties. For example, a process for elastication of a base material layer disclosed in Japanese Patent Publication No. 1998-513070A is adapted to elasticize the base material layer used in an elastic pants-type article. Specifically, the base material layer is provided with elastic members attached thereto so that the elastic members are stretchable in a transverse direction but not in a longitudinal direction in the waist region of the wearing article and stretchable in the longitudinal direction but not in the transverse direction of the wearing article in the crotch region toward a midpoint of which the elastic members contract.

In the known wearing article as has been cited above, the direction in which the elastic members are stretchable in the crotch region must be turned by an angle of 90° with respect to the direction in which the elastic members are stretchable in the waist region. To achieve this, the apparatus as well as the operation is inevitably complicated. In the wearing article obtained by this known process, the crotch region contracts in back-and-forth direction and thereby pulls an absorbent member such as a napkin attached to the inner side of the wearing article upward so as to come in close contact with a wearer's skin. At the same time, such contraction pulls the waist-surrounding upper end zone of the wearing article downward and thereby makes it difficult to stabilize the wearing article on a wearer.

SUMMARY OF THE INVENTION

It is an object of the present invention to provide a process for making a disposable wearing article having a elastically stretchable properies, the process being simplified and improved so that the problem as has been described above may be solved.

According to the present invention, there is provided a process for making an elastically stretchable disposable wearing article which includes a front waist region, a rear waist region and a crotch region extending between the front and rear waist regions all made of an elastically stretchable sheet, transversely opposite lateral marginal zones of the front and rear waist regions being detachably or permanently connected one to another to form a waist-hole and a pair of leg-holes.

The article further includes the wearing article having a first elastic zone formed in a transversely middle zone of the crotch region, a belt-like second elastic zone extending from the first elastic zone parallel to respective peripheries of the leg-holes to respective lateral marginal zones of the front and rear waist regions and third elastic zones defined by remaining zones except the first and second elastic zones wherein the first, second and third elastic zones exhibit a stretch stress adjusted to be decreased in this order.

The process comprising the steps of:
(a) continuously feeding an elastically stretchable web in a machine direction,
(b) forming the web with groups of slits intermittently in the machine direction, each group comprising a plurality slits arranged symmetrically in a cross direction of the web about a transversely middle zone of the web defined by a predetermined dimension in the cross direction,
(c) leaving the middle zone and a portion extending between each pair of the adjacent groups of slits, folding the remaining portion of the web in the cross direction orthogonal to the machine direction so that the remaining portion may be layered so as to be alternately overlapped one upon another,
(d) joining overlapping layers of the web one to another, and
(e) successively cutting the web in the machine direction into a predetermined length.

The present invention may be exploited in preferred manners as follow:

The web is stretched in the machine direction and/or the cross direction and then left to contract in early stage of feeding the web from its roll in the machine direction.

The process further includes a step of joining non-stretchable sheets continuously extending in the machine direction are joined to the lateral marginal zones of the web after the web has been stretched in the machine direction and then left to contract.

The aforesaid step (d) of joining overlapping layers of the web one to another serves also to decrease the elastically stretchable area of the web.

The process further includes a step of attaching belt-like elastic members to zone of the web to form the waist-hole or to form the leg-holes.

DETAILED DESCRIPTION OF THE PREFERRED EMBODIMENTS

Details of a process according to the present invention will be more fully understood from the description given hereunder with reference to the accompanying drawings, taking a holder used to hold a body fluid absorbing article such as a urine-absorbent pad or a sanitary napkin as an example of the disposable wearing article made by the process according to the invention.

Figure 1:
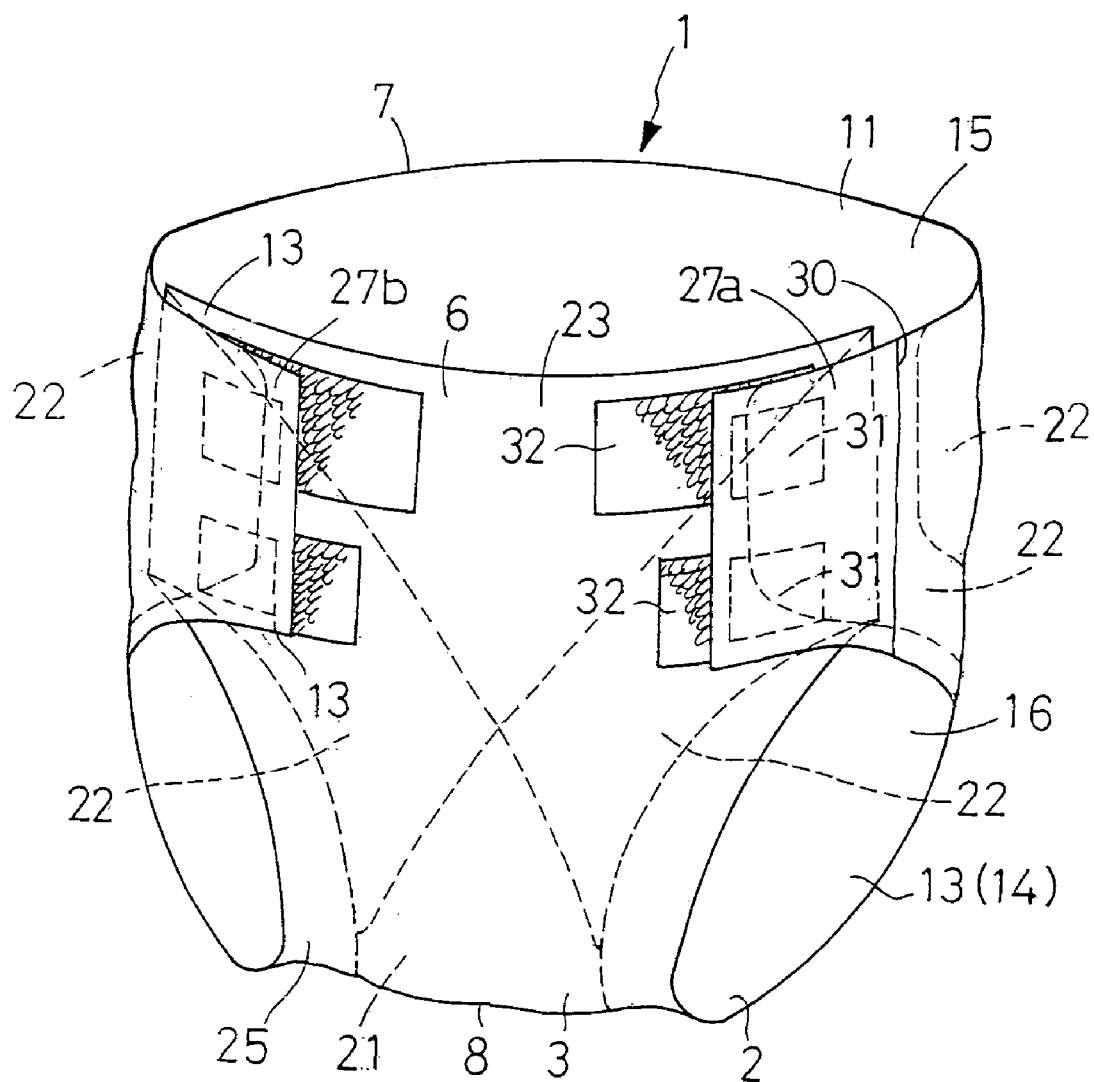
FIG. 1 is a perspective view showing a holder as put on a wearer.
Figure 2:
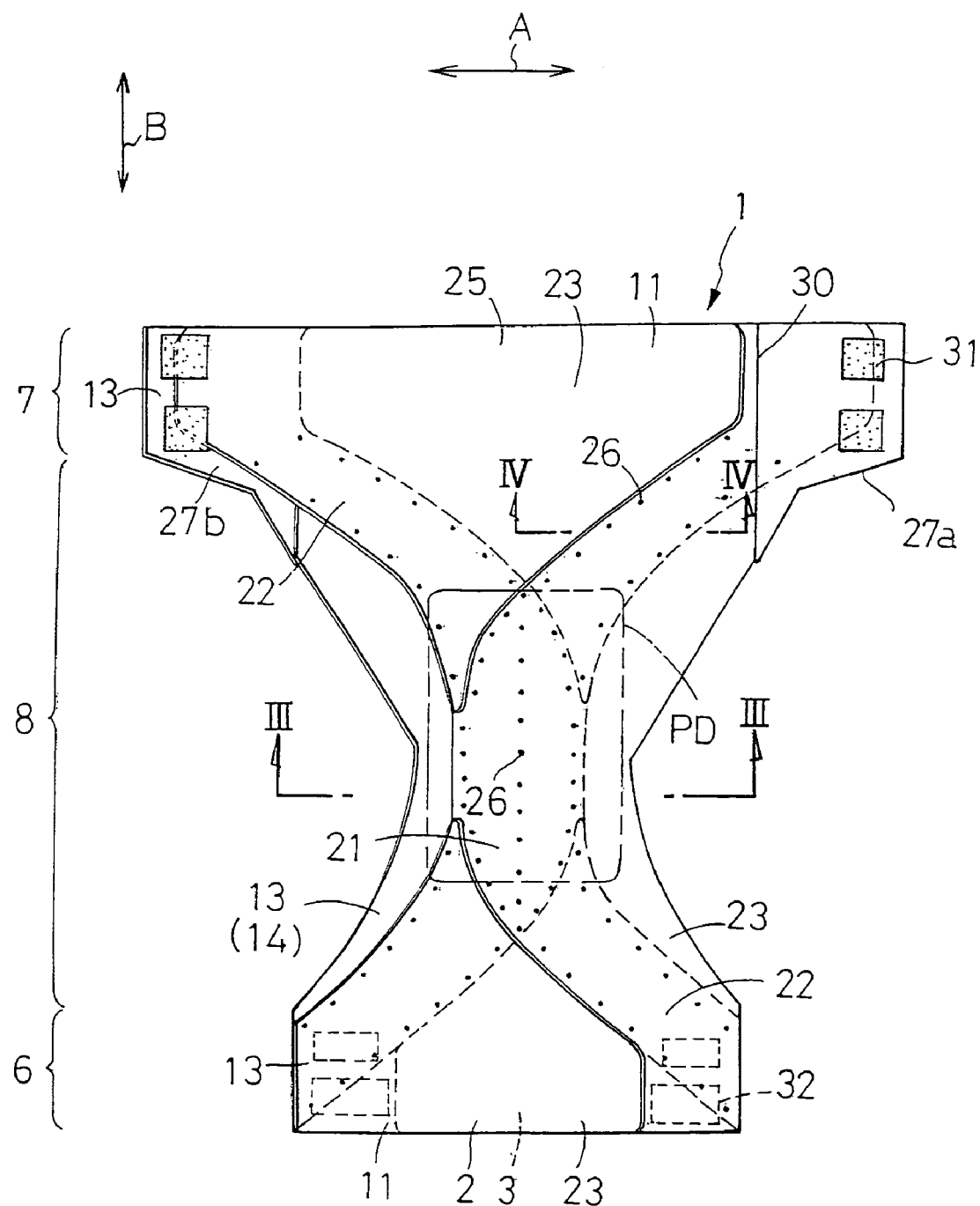
FIG. 2 is a plan view showing a partially cutaway holder.

FIG. 1 is a perspective view showing a holder 1 as put on a wearer and FIG. 2 is a plan view showing a partially cutaway holder 1. The holder 1 is elastically stretchable in a transverse direction as well as in a longitudinal direction respectively indicated by double-headed arrows A and B in FIG. 2 and put on a wearer in order to hold, for example, a urine-absorbent pad PD indicated by an imaginary line in a central zone of FIG. 2 in close contact with a wearer. The illustrated holder 1 presents a generally hourglass-like planar shape and is contoured by front and rear end zones 11 extending in the transverse direction A and lateral marginal zones 13 extending in the longitudinal direction B. As viewed in the longitudinal direction B, the holder 1 defines a front waist region 6, a rear waist region 7 and a crotch region 8 extending between the two waist regions 6, 7. The regions 6, 7, 8 respectively have an inner surface 2 and an outer surface 3. In the crotch region 8, the lateral marginal zones 13 define crotch region's lateral marginal zones 14 describing generally circular arcs which are convex inward. In the front and rear waist regions 6, 7, the lateral marginal zones 13 are provided with mechanical fasteners. More specifically, loop members 32 constituting the mechanical fasteners are attached to the respective lateral marginal zones 13 in the front waist region 6 and hook members 31 constituting the mechanical fasteners are attached to the respective lateral marginal zones 13 in the rear waist region 7. The holder 1 is formed with a waist-hole 15 and a pair of leg-holes 16 as the front and rear waist regions 6, 7 are connected along the lateral marginal zones 13 by means of these mechanical fasteners. As will be apparent from FIG. 2, the holder 1 has a first elastic zone 21 formed in a transversely middle zone of the crotch region 8, belt-like second elastic zones 22 extending from the first elastic zone 21 along the crotch region's lateral marginal zones 14 to the lateral marginal zones 13 in the front and rear waist regions 6, 7, respectively and third elastic zones 23 not inclusive of the first and second elastic zones 21, 22.

Figure 3:
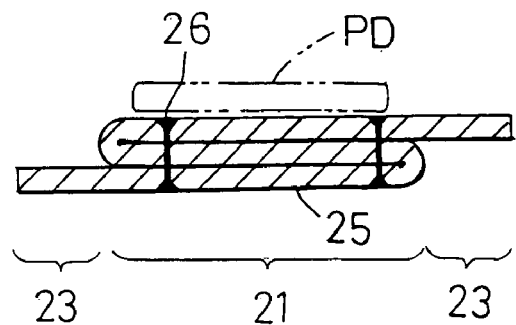
FIG. 3 is a sectional view taken along the line III—III in FIG. 2.
Figure 4:
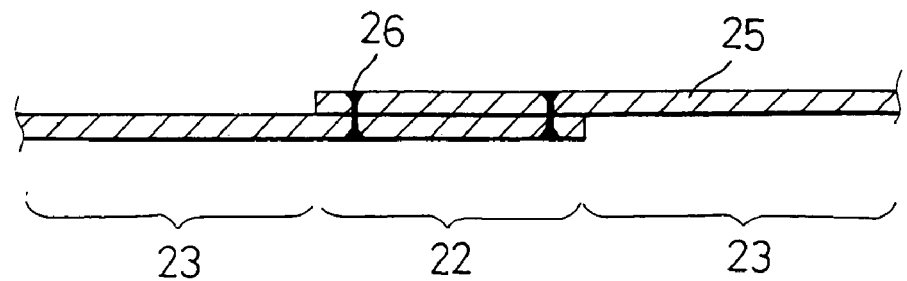
FIG. 4 is a sectional view taken along the line IV—IV in FIG. 2.

FIG. 3 is a sectional view taken along the line III—III in FIG. 2 and FIG. 4 is a sectional view taken along the line IV—IV in FIG. 2. The holder 1 is formed from a sheet 25 having an elastically stretchable properties. The first elastic zone 21 is defined by a three-layered portion of the sheet 25, the second elastic zone 22 is defined by a two-layered portion of the sheet 25 and the third elastic zones 23 are defined by single-layered portion of the sheet 25. Two or three layers of the sheet 25 folded back once or twice are joined one to another by means of heat-sealing or adhesives at a plurality of spots 26 as indicated in FIG. 2. In the transverse direction A and the longitudinal direction B of the holder 1, a stretch stress exhibited by the first elastic zone 21 is higher than a stretch stress exhibited by the second elastic zone 22 and the stretch stress exhibited by the second elastic zone 22 is higher than a stretch stress exhibited by the third elastic zones 23.

With the holder 1 put on a wearer as shown in FIG. 1, the second elastic zone 22 extending to the lateral marginal zones 13 in the front waist region 6 and the second elastic zone 22 extending to the lateral marginal zones 13 in the rear waist region 7 are placed one and another in the vicinity of the waist's lateral marginal zones 13. The second elastic zones 22 in the front and rear waist regions 6, 7 cooperate with the first elastic zone 21 in the crotch region 8 to define annular elastic zones which are stretchable around wearer's thighs, respectively. Contraction of the first and second elastic zones 21, 22 in reaction to stretching thereof in a leg-surrounding direction functions to uplift the urine-absorbent pad PD placed in the crotch region 8 toward a wearer'scrotch region and thereby to hold the pad PD in close contact with a wearer. It should be noted here that these first and second elastic zones 21, 22, particularly the second elastic zones 22 contracts not in the vertical direction but in the leg-surrounding direction. Therefore, the holder 1 is position-stabilized on a wearer without the anxiety that the holder 1 might slip down along a wearer due to contraction of the first and second elastic zones 21, 22.

FIGS. 5 through 10 are diagrams each partially illustrating main steps of the process for continuously making a plurality of the holders 1 from a web 125 corresponding to the continuous sheet 25.

Figure 5:
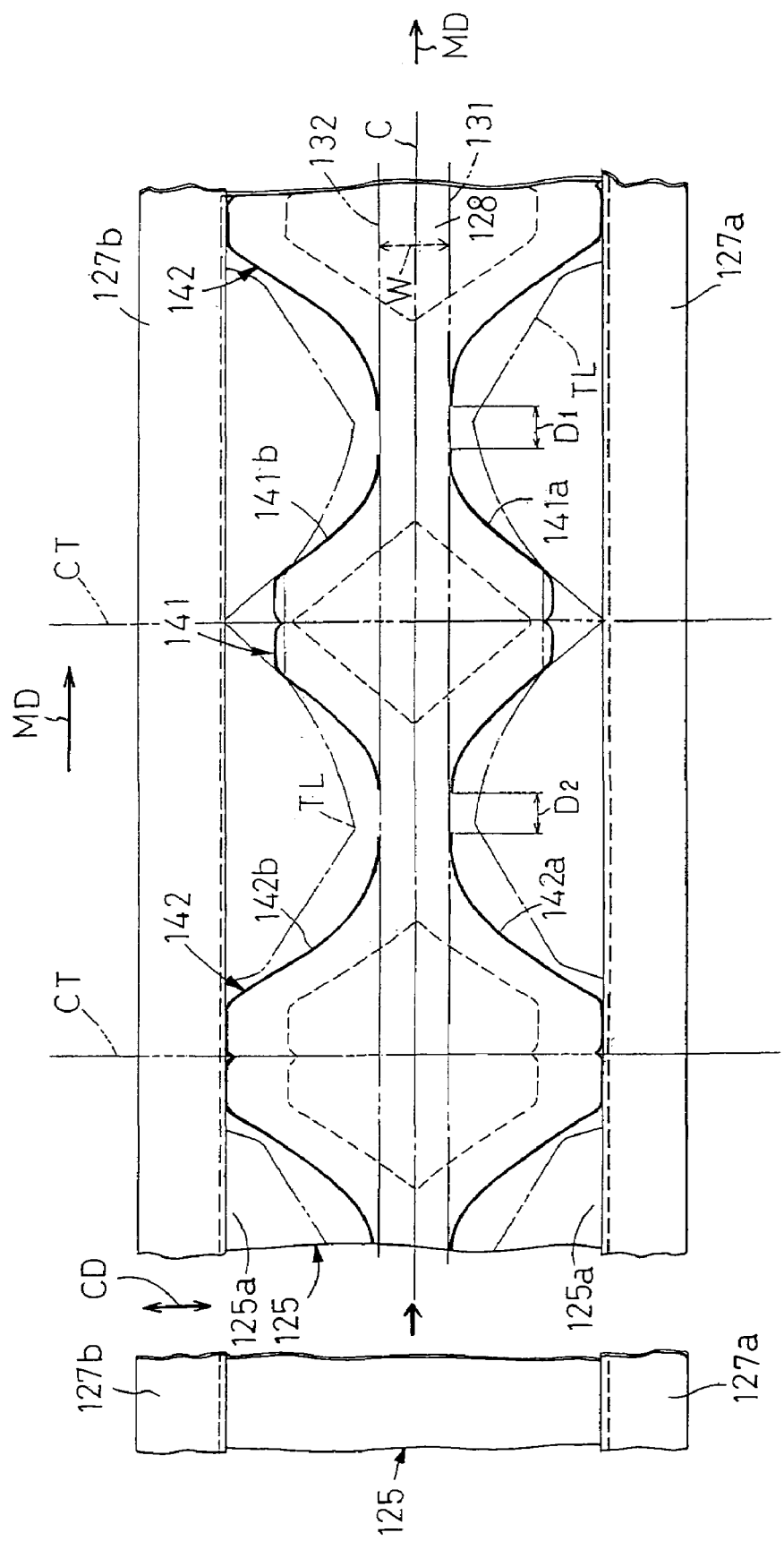
FIG. 5 is a diagram partially illustrating a process for making the holder.

In FIG. 5, an arrow MD designates a machine direction and an arrow CD designates a cross direction which is orthogonal to the machine direction MD. The web 125 continuously fed in the machine direction MD is elastically stretchable in the machine direction MD as well as in the cross direction CD. Continuous sheets 127a, 127b which are non-stretchable in the machine direction MD are joined to transversely opposite side edge zones 125a of the web 125, respectively, in order to suppress stretchability of the web 125 in the machine direction MD. First and second imaginary lines 131, 132 extending in parallel to a center line C bisecting a width of the web 125 and being equidistant from this center line C define therebetween a transversely middle zone 128 having a predetermined width W in the transverse direction of the web 125. Outside this middle zone 128, first pairs of slits 141 and second pairs of slits 142 arranged intermittently in the machine direction MD. Each first pair of slits 141 comprise a first lower slit 141a and a first upper slit 141b formed symmetrically about the middle zone 128. Each second pair of slits 142 comprise a first lower slit 142a and a first upper slit 142b formed symmetrically about the middle zone 128. In the illustrated embodiment, the first pair of slits 141 are formed in a pattern different from a pattern in which the second pair of slits 142 are formed. The second pair of slits 142 are spaced apart from the first pair of slits 141 by a distance $D_1$ and the first pair of slits 141 are spaced apart from the second pair of slits 142 by a distance $D_2$ in the machine direction MD.

Of the web 125 illustrated in FIG. 6, the portion extending below the first lower slit 141a, the portion extending below the second lower slit 142a and the portion extending in the machine direction between these two slits 141a, 142a are folded along the first imaginary line 131 upward as indicated by an arrow P.

Figure 6:
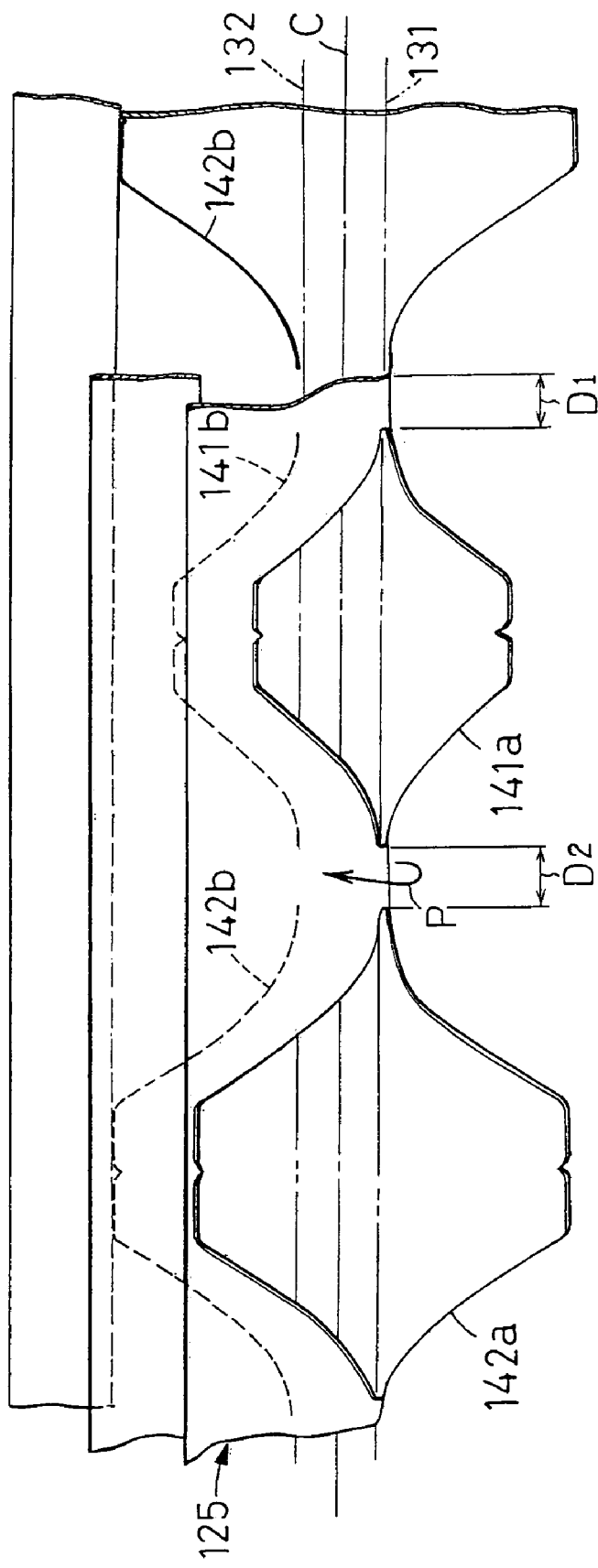
FIG. 6 is a diagram partially illustrating the process for making the holder.
Figure 7:
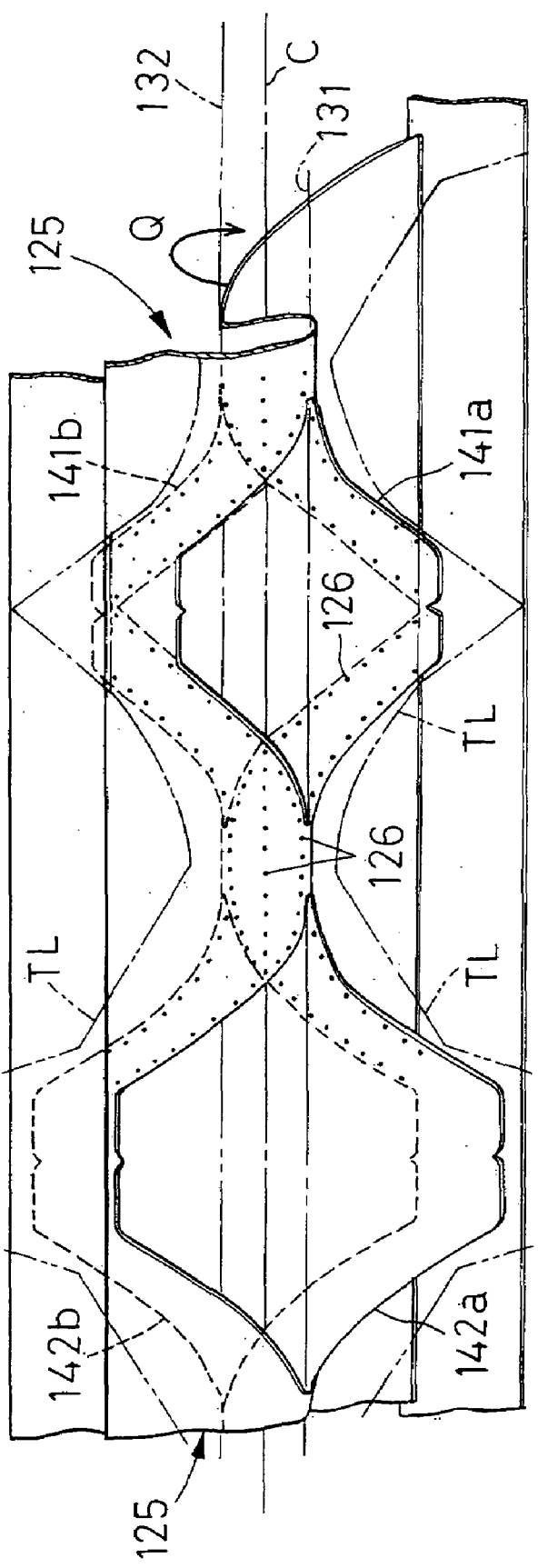
FIG. 7 is a diagram partially illustrating the process for making the holder.

Of the web 125 illustrated by FIG. 7, the portion extending above the first upper slit 141b, the portion extending above the second upper slit 142b and the portion extending in the machine direction MD between the two slits 141b, 142b are folded along the second imaginary line 132 downward as indicated by an arrow Q so that these portions folded downward and those portions having already been folded upward as illustrated in FIG. 6 may be alternately overlapped one another about the transversely middle zone 128. Zones in which the portions folded as illustrated in FIG. 6 overlap the portions folded as illustrated in FIG. 7 are joined together at a plurality of spots 126 by means of heat-sealing or adhesives to prevent these zones from shifting relative to each other.

Figure 8:
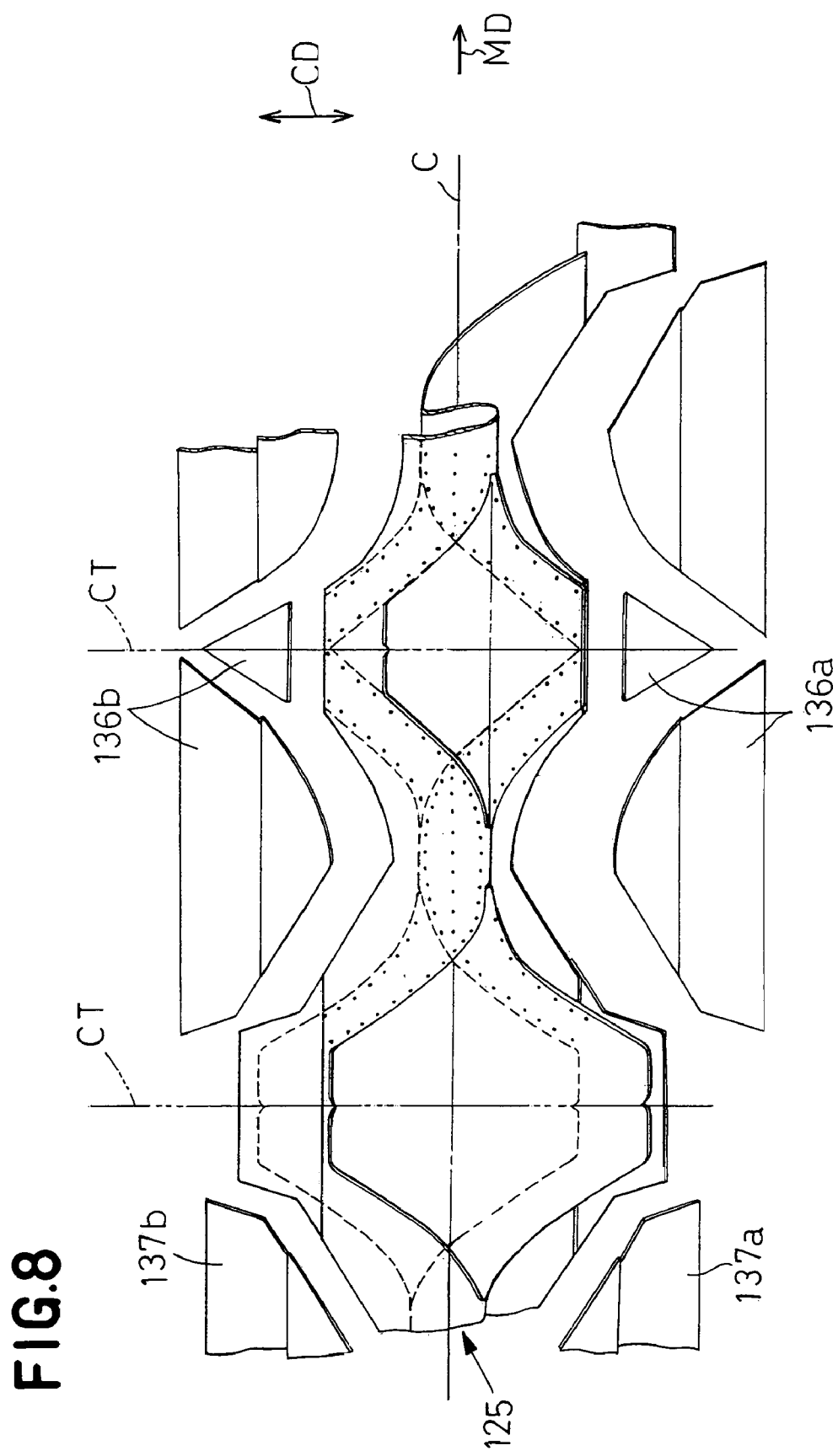
FIG. 8 is a diagram partially illustrating the process for making the holder.

Referring to FIG. 8, unwanted portions 136a, 136b, 137a, 137b are cut away from the web 125 in a state as illustrated by FIG. 7 along trim lines TL indicated by chain double-dashed lines in FIGS. 5 and 7.

Figure 9:
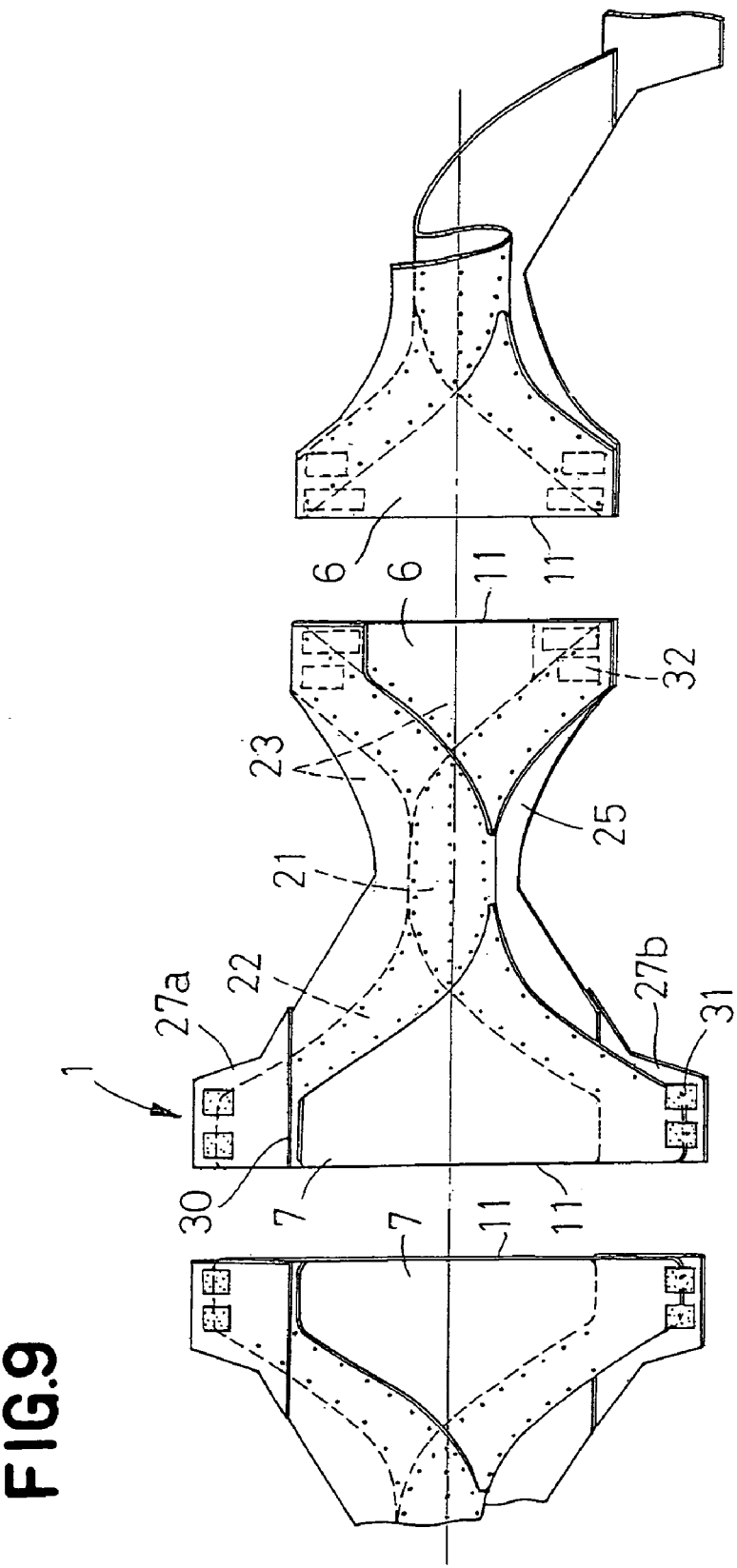
FIG. 9 is a diagram partially illustrating the process for making the holder.

Referring to FIG. 9, the web 125 is cut intermittently as viewed in the machine direction MD along cut lines CT extending in the cross direction CD as indicated by chain triple-dashed lines in FIG. 8. Each of the individual sections obtained by cutting the web 125 in this manner is provided on its inner surface (i.e., front side of illustration) at predetermined positions with hook members 31 constituting the mechanical fastener and on its outer surface (i.e., backside of illustration) at predetermined positions with loop members 32 constituting the mechanical fastener. The hook members 31 and loop members 32 are respectively joined to the individual sections of the web 125 to form blanks of the holders 1 shown by FIG. 1. As will be understood from FIG. 5, the cut lines CT extend in the cross direction CD so as to bisect the first pair of slits 141 as well as the second pair of slits 142 in the machine direction MD.

In the course of steps illustrated by FIGS. 5 through 9, a plurality of the holders 1 are continuously made, i.e., with the end zones 11 of the front waist regions 6 connected one to another and the end zones 11 of the rear waist regions 7 connected one to another and then each pair of the adjacent end zones 11 are cut off along the cut line CT. It should be noted here that, in the illustrated holder 1, there remain small sections 27a, 27b of the continuous sheets 127a, 127b along the lateral marginal zones of the rear waist region 7 (See FIG. 9) and the small sections 27a, 27b define wings in the rear waist region 7. Lines 30 appearing along proximal ends of the respective wings are lines along which the sheet 25 is bonded to the sections 27a and 27b, respectively (See FIG. 1 also).

Figure 10:
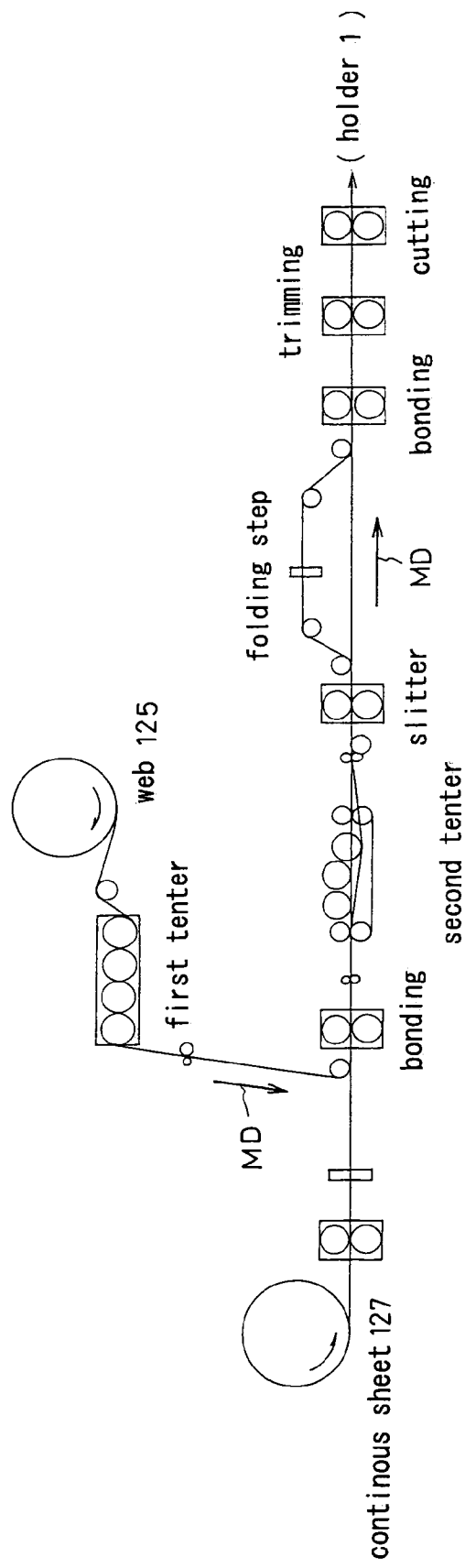
FIG. 10 is a diagram illustrating the entire process for making the holder.

FIG. 10 is a diagram illustrating substantially entire process for making the holders 1. Though not clearly illustrated, this diagram should be understood to include the steps illustrated in FIGS. 5 through 8. The continuous web 125 destined to form the elastically stretchable sheet 25 is fed from above as viewed in the diagram. The web 125 is fed forward from its roll in the machine direction MD, then stretched by a first tenter in the machine direction MD and contracts. The non-stretchable belt-like continuous sheets 127 are fed from the left hand as viewed in the diagram onto the transversely opposite lateral marginal zones of the web 125 and joined thereto. Subsequently the web 125 is stretched by a second tenter in the cross direction CD, then contracts and travels to the folding step illustrated by FIGS. 5 through 8. The web 125 folded and fixed in this folded state by joining the layers of this folded web 125 one to another is then trimmed, cut intermittently in the machine direction MD and provided at the predetermined positions with the mechanical fasteners 31, 32 (See FIG. 9) joined thereto. In this manner, a plurality of the holders 1 continuously are made.

In the process for making such holders 1, the continuous sheets 127a, 127b are used substantially for the purpose of suppressing stretch of the web 125 in the machine direction MD but not necessarily for the purpose of leaving the wings. From such viewpoint, it is also possible to consider that the holder 1 substantially comprises the elastically stretchable single sheet 25. In this holder 1, regardless of this, the sheet 25 is folded so that the sheet 25 is three-layered in the transversely middle zone of the crotch region 8 to define the first elastic zone 21, two-layered in the front and rear waist regions 6, 7 to define the second elastic zone 22 extending generally in X-shape and single-layered in the remaining zones to define third elastic zones 23. In this way, the stretch stress exhibited by the holder 1 can be differentially adjusted depending on the respective regions or zones. While the web 125 can be made free from any undesirable tendency as the web 125 is stretched by the first and second tenters in the longitudinal direction as well as in the transverse direction and then contract in these directions in this process, the step of stretching the web 125 by the first and second tenters may be eliminated even when the web 125 is fed from its roll, so far as the web 125 is initially free from any undesirable tendency.

Figure 11:
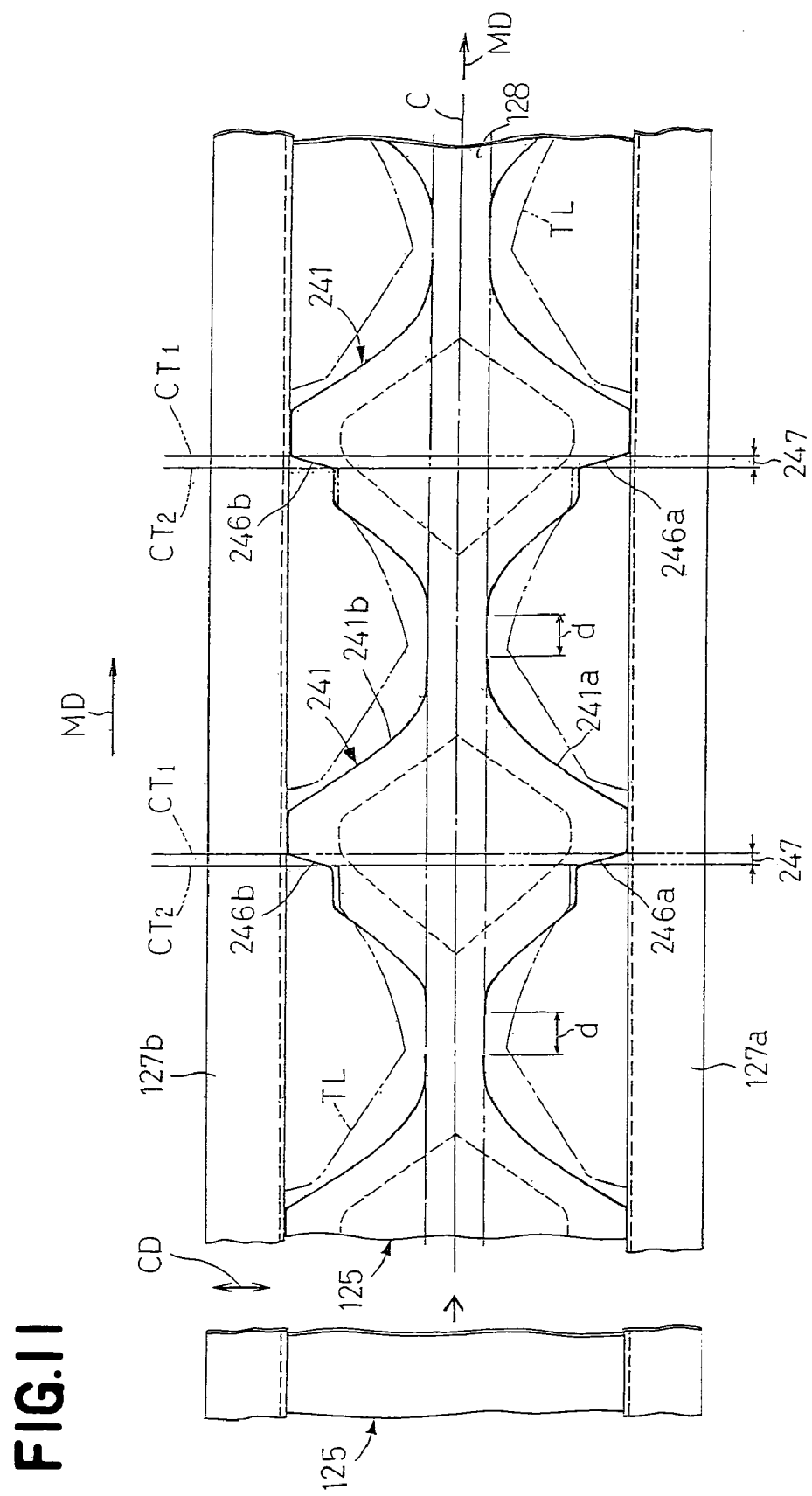
FIG. 11 is a diagram similar to FIG. 5, illustrating one preferred embodiment of the invention.
Figure 12:
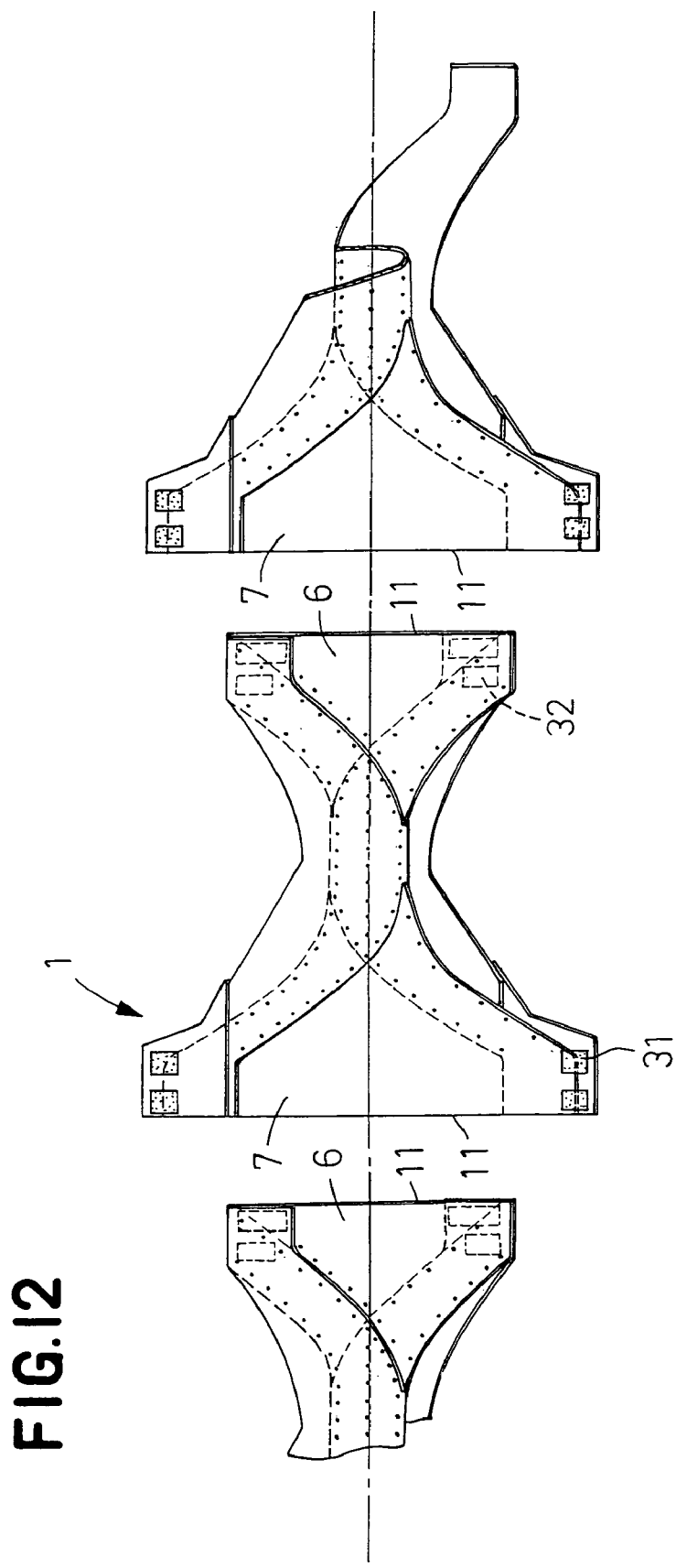
FIG. 12 is a diagram similar to FIG. 9, illustrating another preferred embodiment of the invention.

FIGS. 11 and 12 are diagrams similar to FIGS. 5 and 6, respectively, illustrating another embodiment of the invention. In the process according to this embodiment, the web 125 including the continuous sheets 127a, 127b joined thereto is formed with the first pairs of slits 241 intermittently in the machine direction MD and each of these first pairs of slits 241 comprise the first lower slit 241a and the first upper slit 241b are symmetrically formed about the middle zone 128. The first pair of slits 241 is spaced apart from the adjacent first pair of slits 241 by a distance d. Similarly to the case illustrated by FIGS. 6 through 8, the web 125 is folded, joined, has the unwanted sections cut off and then cut along the cut lines $CT_1$ and $CT_2$ extending parallel to each other in the cross direction CD as seen in FIG. 11. Before or after cutting step, the hook members 31 and the loop members 32 are bonded to the web 125 and the holder 1 as shown by FIG. 1 can be obtained from such web 125. The process according to this embodiment is distinguished from the embodiment of the process illustrated by FIGS. 5 through 9 in that the end zone 11 of the front waist region is contiguous to the end zone 11 of the rear waist region 7 to form a plurality of the holders 1 contiguous one to another. Referring to FIG. 11, the sections to form the front and rear waist regions 6, 7 are connected with each other by connector slit sections 246a, 246b respectively forming respective parts of the first lower slit 241a and the first upper slit 241b. The web 125 is cut along the adjacent cut lines $CT_1$, $CT_2$ between which the connector slit sections 246a, 246b obliquely extend and thereby unwanted sections 247 defined between these two adjacent cut lines $CT_1$, $CT_2$ are cut away to obtain the holder 1 illustrated in FIG. 12. It is possible to cut the web 125 only along the cut line $CT_2$ without cutting the unwanted section 247 away, then to fold the unwanted section 247 back along the cut line $CT_2$ onto the rear waist region 7 of the holder 1 and to join this section 247 thereto. It is also possible to provide the web 125 illustrated in FIG. 11 with no unwanted section 247 and to connect the first lower slit 241a is made contiguous directly to the first upper slit 241b, so that the cut lines $CT_1$, $CT_2$ may fall into line.

The process according to the present invention allows shapes of the first and second elastic zones 21, 22 in the holder 1 to be selectively varied by varying shapes of the respective slits in the first pair of slits 141, 241 and of the respective slits in the second pair of slits 142. A stretch stress of the first and second elastic zones 21, 22 can be selectively varied by varying a total area of the spots 26 per unit area of the sheet 25 in the holder 1. While the step of folding the web 125 illustrated by FIGS. 5 through 8 is generally facilitated by joining the non-stretchable continuous sheets 127a, 127b to the transversely opposite lateral marginal zones 125a, the present invention can be implemented also without using such continuous sheets 127a, 127b. In the holder 1, the first elastic zone 21 exhibits the highest stretch stress and tensile strength and therefore this zone 21 may be formed with a through-hole and a peripheral inner surface 2 of this through-hole may be formed with a flexible and elastically compressive bulge while a peripheral outer surface 3 of this through-hole may be formed with a pocket adapted to receive bodily discharges such as loose passage to use the holder 1 as a disposable diaper for taking care of feces. The holder 1 may be combined with the urine-absorbent pad PD or an appropriate bodily fluid absorbent pad other than the urine-absorbent pad PD to use this holder 1 as a disposable diaper cover or the wearing article serving to hold disposable diaper or sanitary napkin in close contact with a wearer. Furthermore, the lateral marginal zones 13 in the front and rear waist regions 6, 7 of the holder 1 may be bonded one to another by means of adhesives or heat-sealing to obtain a pants-type holder 1. The process for making such pants-type holder 1 is also covered by the present invention. In any embodiment of the holder 1, the waist elastic members and the leg elastic members may be attached to the waist's lateral marginal zones and the legs' lateral marginal zones, respectively, in a stretched or non-stretched state.

The process according to the present invention allows the disposable wearing article having a high stretch stress in the crotch region to be obtained merely by folding the elastically stretchable single sheet.

What is claimed is:

1. A process for making an elastically stretchable disposable wearing article which includes a front waist region, a rear waist region and a crotch region extending between these waist regions all made of an elastically stretchable sheet, wherein transversely opposite lateral marginal zones of said front and rear waist regions detachably or permanently connected one to another to form a waist-hole and a pair of leg-holes, and further includes a first elastic zone formed in a transversely middle zone of said crotch region, a belt-like second elastic zone extending from said first elastic zone in parallel to respective peripheries of said leg-holes to respective lateral marginal zones of said front and rear waist regions and third elastic zones defined by remaining zones except for said first and second elastic zones wherein said first, second and third elastic zones exhibit a stretch stress adjusted to be decreased in this order; said process comprising the steps of:

(a) continuously feeding an elastically stretchable web in a machine direction, (b) forming said web with groups of slits intermittently in the machine direction, each group comprising a plurality of slits arranged symmetrically in a cross direction of said web about a transversely middle zone of said web defined by a predetermined dimension in the cross direction, (c) leaving said middle zone and a portion extending between each pair of the adjacent groups of slits, folding a remaining portion of said web in the cross direction orthogonal to said machine direction so that said remaining portion may be layered so as to be alternately overlapped one upon another, (d) joining overlapping layers of said web one to another, and (e) successively cutting said web in the machine direction into a predetermined length to form said first, second and third elastics zones.

2. The process according to claim 1, wherein, said web is stretched in said machine direction and/or said cross direction and then left to contract in early stage of feeding said web from its roll in said machine direction.

3. The process according to claim 2, further including a step of joining non-stretchable sheets continuously extending in said machine direction are joined to the lateral marginal zones of said web after said web has been stretched in said machine direction and then left to contract.

4. The process according to claim 1, wherein said step (d) of bonding overlapping layers of said web one to another serves also to decrease the elastically stretchable area of said web.

* * * * *